(12) United States Patent
Cutler et al.

(10) Patent No.: US 7,541,587 B2
(45) Date of Patent: Jun. 2, 2009

(54) GAS SENSOR

(75) Inventors: Stuart Christopher Cutler, Hampshire (GB); Alexander Vass, Hampshire (GB)

(73) Assignee: City Technology Limited, Portsmouth (GB)

( * ) Notice: Subject to any disclaimer, the term of this patent is extended or adjusted under 35 U.S.C. 154(b) by 132 days.

(21) Appl. No.: 10/580,671

(22) PCT Filed: Dec. 1, 2004

(86) PCT No.: PCT/GB2004/005035

§ 371 (c)(1),
(2), (4) Date: May 26, 2006

(87) PCT Pub. No.: WO2005/054827

PCT Pub. Date: Jun. 16, 2005

(65) Prior Publication Data

US 2007/0102639 A1    May 10, 2007

(30) Foreign Application Priority Data

Dec. 2, 2003   (GB)   ................................. 0327931.2

(51) Int. Cl.
G01N 21/61 (2006.01)
G01J 1/00 (2006.01)

(52) U.S. Cl. ............................ 250/339.13; 250/339.14; 250/341.1; 250/343; 73/23.4

(58) Field of Classification Search ....................... None
See application file for complete search history.

(56) References Cited

U.S. PATENT DOCUMENTS

| 3,614,431 A | 10/1971 | Low |
| 5,475,222 A | 12/1995 | King |
| 5,495,747 A * | 3/1996 | Herman et al. ............. 73/23.21 |
| 5,721,430 A * | 2/1998 | Wong ..................... 250/339.13 |
| 6,410,918 B1 | 6/2002 | Kouznetsov |
| 6,469,303 B1 | 10/2002 | Sun et al. |
| 6,989,549 B2 * | 1/2006 | Diekmann et al. .......... 250/573 |
| 2002/0153490 A1 | 10/2002 | O'Leary |
| 2004/0209507 A1 * | 10/2004 | Starta et al. ................. 439/247 |

FOREIGN PATENT DOCUMENTS

| DE | 201 21 183 U1 | 4/2003 |
| DE | 203 01 081 U1 | 4/2003 |
| EP | 0896216 | 2/1999 |
| GB | 2116317 | 9/1983 |
| GB | 2 316 172 A | 2/1998 |
| GB | 2372099 | 8/2002 |
| WO | WO 02/077619 | 10/2002 |
| WO | WO 2004/023113 | 3/2004 |

OTHER PUBLICATIONS

Rogalski, A. et al., "Infrared devices and techniques", Opto-Electronics Review, vol. 10, No. 2, 2002, pp. 111-136.*

* cited by examiner

*Primary Examiner*—David P Porta
*Assistant Examiner*—Yara B Green

(57) ABSTRACT

A gas sensor comprises a cavity for containing a gas, means for generating radiation which is transmitted through the cavity and includes one or more wavelengths which is absorbed in use by a gas to be detected; and a detector for detecting radiation which has passed through the cavity. The walls of the cavity are sufficiently reflective to the radiation that the cavity is substantially uniformly illuminated with the radiation.

46 Claims, 2 Drawing Sheets

GAS SENSOR

The application is directed towards the design of small gas sensors which monitor the absorption of radiation, typically infra-red radiation, to detect the presence of a gas, particularly for use in portable equipment.

Examples of such sensors employ the principle of non dispersive infra-red (NDIR) dual beam absorption spectroscopy. A detector provided with a wavelength selective filter whose pass band substantially overlaps an infra red absorption feature of the target gas measures the radiation transmitted after passage through the atmosphere to be examined. Usually, a second detector, provided with a filter whose pass band is substantially free from any spectral overlap with the target gas, provides a reference measurement. By ratioing the signals received by the two detectors when illuminated by a broadband source of radiation, an output which in principle depends only upon the radiation absorbed by the target gas may be obtained. With additional knowledge concerning the effective pathlength of the system, and the temperature and pressure of the gas, this ratiometric output may be directly correlated to the concentration of the target species. The gas is not consumed nor otherwise chemically altered by these absorption processes.

There have been many attempts to address the challenges presented by the requirement to minimise sensor size, cost and power consumption whilst providing performance which is capable of meeting the demands of safety critical applications for the detection of toxic and/or combustible gases. However, none of these offers a complete solution to the difficulties encountered. In particular, designing and manufacturing relatively low cost systems offering good sensitivity but also having stable performance over long periods and wide temperature ranges has proved a major challenge. It is important that the design has good tolerance towards changes in physical dimensions and optical properties which unavoidably occur as sensors are operated in harsh environments across a wide range of ambient conditions.

In GB-A-2316172, a chamber containing the gas to be detected also acts as an optical system whose surfaces are curved so as to reflect light emitted from a source at least three times before reaching the detector. This is essentially an imaging system, so that in order to work efficiently, both the source and detector must be placed very close to the foci of the curved reflective surfaces. This requirement places significant demands upon the accuracy of manufacture/assembly, and especially on the maintenance of the component positions as a function of temperature. (In the intended applications, it is very unlikely that the temperature of the entire assembly can be controlled due to power consumption considerations). In addition, the chamber design (size and curvatures) must be significantly altered in order to produce the different pathlengths which are required for the optimum detection of various species.

In U.S. Pat. No.-B-6,469,303, the approach is to utilize only the reflective inner surface of a cylindrical housing to focus light from the source on to the detector, the upper and lower end faces being non-reflective. The light path is thus predominantly in the plane of the cylinder cross section. This produces an imaging system in which a comparatively small fraction of the available internal volume is utilised for the light path and in this respect the design is space inefficient. There would also be concerns regarding the stability of the focussing arrangement with age and temperature.

In these and other examples, considerable effort is taken to ensure that the source is reasonably accurately imaged on to the detector. Two aspects or advantages are normally cited for such an approach.

(a) An accurately imaged source indicates that the system efficiently uses the available optical energy ie that a large fraction of radiation emitted by the source reaches the detector and can therefore contribute to the received signal.

(b) In an imaging system, rays passing from the source to the detector nominally traverse very similar pathlengths through the gas. Knowing the absorption properties of the target species, a direct relationship can theoretically be established between the observed signal and the gas concentration.

An alternative approach is described in GB-A-2372099 in which the source is mounted toward the outside of the cylindrical package with the detector in the centre. The optical path is an annular light pipe or light guide and so relies on multiple reflections at relatively high angles of incidence to direct light toward the detector, with an angled reflector to finally direct the radiation radially inwards. However, this approach does not offer particularly efficient illumination of the detector and places great dependence upon the stability of the final angled reflector to maintain good performance. Again, modification of the pathlength is not readily achieved and in addition, the high angles of incidence and large number of reflections in the reflective path attenuate the radiation and are particularly prone to changes caused by surface contamination.

In accordance with a first aspect of the present invention, a gas sensor comprises a cavity for containing a gas; means for generating radiation which is transmitted through the cavity and including one or more wavelengths which is absorbed in use by a gas to be detected; and a detector for detecting radiation which has passed through the cavity, the walls of the cavity being sufficiently reflective to the radiation that the cavity is substantially uniformally illuminated with the radiation.

Our design utilises the fact that the source power and detector sensitivities of standard low cost components is adequate to allow successful operation in a non-focusing mode. We purposely avoid imaging of a source or the use of a light guide to convey the radiation from source to detector and aim to produce uniform illumination in the region occupied by the detector(s). This approach largely overcomes the undesirable sensitivity of imaging systems to mechanical, thermal and wavelength-dependent changes. Our approach is highly tolerant to such changes and produces good performance at moderate price.

We have realized that the apparent need to focus images on to detectors can be relaxed. Thus, aspect (a) above is of less importance in systems where the main limitation on performance is not defined by the low intensity of light falling on the detector; ie where received power levels across the intended range of absorption are well above the noise levels of the detector. The production of an accurate image requires relatively complex and expensive optics, particularly when multiple images are necessary (as in systems employing signal and reference channels). Furthermore, mechanical movements induced by temperature and ageing of the system can cause the image to move in relation to the detector, leading to sensitivity variations which can be very difficult to compensate in practice.

In the case of aspect (b), we have found in practice that the relatively wide variations which are likely to occur in source power and detector sensitivity mean that individual device calibration is invariably required. Furthermore, it is our experience that the drift in sensor characteristics which occur as a function of age, temperature, surface contamination/obscuration and other parameters are more severe when the design relies on imaging or light guiding that conducts the radiation directly from source to detector.

The sensor comprises a gas sensing cell which also acts as an optical cavity bounded on substantially all sides by highly reflective walls (although some areas may comprise low reflectivity material, or have their highly reflective coatings obscured in order to specifically tailor the propagation of light). The reflectivity of the walls may be specular or diffuse and the cavity may comprise any number of flat, cylindrical, spherical or conic sections, but simple forms may be spherical, cubic or cylindrical with flat closures at both ends. The cavity can have any convenient shape provided its interior is substantially uniformly illuminated.

Preferably, the detector has a surface area which is visible to the interior of the cavity, and the walls of the cavity are sufficiently reflective to the radiation that the visible surface area of the detector is illuminated with substantially unfocussed radiation. Further preferably, the entire visible surface area of the detector is illuminated with substantially unfocussed radiation. The visible area of the detector is also termed its "active area". In a substantially uniformly illuminated cavity, the radiation is unfocussed which leads to the sensor construction itself having characteristics quite different from those of the known, focused, systems. Important considerations include the ratio of the area of the cavity walls (the illuminated surface) to the active area of the detector, and the ratio of the power of the radiation source to the area of the cavity walls.

Preferably, the sensor design is such that increasing the visible surface area of the detector relative to the surface area of the cavity walls increases the signal to noise ratio detected by the detector. This is because, in an unfocussed system if the sensor designer increases the illuminated surface area of the cavity (for example because he wishes to increase the enclosed gas volume or, more likely, the effective pathlength of the system), then either the detector area or the source power must increase individually or in combination in order to maintain the same signal to noise ratio on the detector output (which is a useful quality parameter for the overall performance). Conversely, if the cavity surface area is increased without any other changes, then although the pathlength rises, the signal to noise level in the detected signal will decrease until the device no longer represents a viable gas sensor.

We can illustrate this point in a different way. In a focusing optical system, such as those mentioned above, it would be detrimental to increase the detector area without making any other design changes. If a given detector area properly receives the focused light, then increasing the active area will not contribute to the desired signal, but will produce increased background noise. However, in a sensor having substantially uniform illumination, a larger detector in an otherwise unaltered system will collect an increased fraction of the radiation and therefore improve the signal to noise ratio. This generalization is of course subject to practical limitations imposed by, for example (i) the scaling of detector performance parameters as the active area increases; (ii) the effect of reducing the reflecting (as opposed to detecting) area of the gas cavity on the uniformity of the radiation. In view of these factors, a compromise must be reached and a specific ratio of active detector area to cavity wall area may be preferable. This should provide high signal to noise ratio whilst not affecting the uniformity of the radiation significantly.

A further difference exists in that in an ideal, evenly illuminated system, all the internal optical surfaces of the cavity are "active" in that they all contribute (equally) to the performance of the sensor. In a focusing system, on the other hand, it is generally true that not all of the optical surfaces are "active" in this regard. Here, only a small fraction of the total surface is illuminated, indicative of a quite different arrangement to that which we describe. Moreover, in focussing systems, the surfaces must be specularly reflective in order to direct the light beams appropriately. In the uniformly illuminated system of the present invention, on the other hand, the cavity walls need not be specular and may even preferentially be scattering (diffuse).

One manner in which uniform illumination may be achieved is via careful control of the cavity dimensions. In an ideal situation, the cavity would be in the form of an integrating sphere, which effectively homogenizes the radiation. However, machined highly reflective spheres do not lend themselves to low cost manufacture as demanded by the industry. Cylindrical chambers offer much better manufacturability. In one advantageous embodiment, the cavity comprises a first end wall adjacent to which at least one of the means for generating radiation and the detector is positioned, a second end wall which opposes the first end wall, and a side wall; the first and second end walls defining the height of the cavity between them and the width of the cavity being defined as a maximum dimension of the cavity orthogonal to its height, wherein the ratio of the height to the width is greater than or equal to 0.1. The cavity height is typically measured as the maximum distance between the end walls, parallel to the normal of one (or both) of the end walls.

Where the radiation source and detector are positioned on the same side of the cavity, as is preferable, the dimensions of the cavity may alternatively be defined with reference to these components. As such, the cavity comprises a first end wall adjacent to which the means for generating radiation and the detector are positioned, a second end wall which opposes the first end wall, and a side wall; the width of the cavity being defined as the maximum dimension of the cavity along a line joining the means for generating radiation and the detector, and the height of the cavity being defined as the maximum dimension of the cavity in a direction orthogonal to its width, wherein the ratio of the height to the width is greater than or equal to 0.1. For clarity, the above mentioned ratios are the height of the cavity divided by its width.

Preferably, the height to width ratio is greater than or equal to 0.2. More preferably, the height to width ratio is greater than or equal to 0.4, preferably approximately 0.46. Further preferably, the height to width ratio is greater than or equal to 0.5. Preferably, the height to width ratio is less than or equal to 2. More preferably, the height to width ratio is less than or equal to 1 (that of a spherical cavity). Further preferably, the height to width ratio is less than or equal to 0.7.

Such aspect ratios have been found to result in substantially uniform illumination of radiation in the cavity as is sought for the above-described reasons. In particular, we have found that relatively low, flat cylindrical cavities are a good approximation to the ideal spherical cavity in that they produce substantially uniform illumination and are free from the tendency of long thin lightpipes to bundle radiation towards the centre of their circular cross-section. It should be noted that in practically implementing the concept of substantially uniform illumination, cavities having relatively even dimensions in all directions are preferable, but that the extent to which this is achievable is modified by practical considerations.

The invention is primarily concerned with the use of infrared (IR) radiation and will be described in this context below. However, it is feasible to utilize other wavelengths providing suitable sources/detectors and reflective materials are employed.

The preferred implementation is a cylindrical surface closed at each end by a flat disk. This arrangement is not intended to produce an image of the source at the detector. Rather, the cavity is intended to act as combination of a light guide and an integrator, designed to provide a much more uniform distribution of light over the reflecting surface than would normally be the case in an imaging system. This approach gives better reproducibility between devices of notionally the same design and minimises the requirement for individual linearisation and compensation algorithms. This tolerance of wavelength-dependent parameter shifts is achieved at the expense of total optical throughput or efficiency, but in sensor systems of the type discussed here, this is a beneficial trade-off.

The performance of a sensor based on a cylindrical chamber closed by plane faces is dependent upon a number of design aspects.

(1) The height and diameter (width) of the cavity.

A complex relationship describes the effect of these parameters upon the effective pathlength of the system. More generally, the performance of any such system will be governed, in part, by the impact of the size and shape of the cavity upon the effective pathlength. If the substantially uniform illumination is implemented by the cavity shape, it can be important to select the cavity dimensions carefully.

(2) The size, shape and position of the openings in the cavity.

Openings in the cavity (and the resultant loss of effective reflective surface area) help to determine the effective path length through the gas. Openings are provided for the admission and egress of gas and electromagnetic radiation. The minimum requirement is that there should be one hole in the cavity to allow gas and electromagnetic radiation to enter and leave the cavity. The openings used for admitting and extracting radiation may be covered by transparent windows or optical filters in order to select the type of radiation admitted to or extracted from the cavity. The openings for the admission of gas are preferentially sited in areas where, due to the geometry of the cavity, electromagnetic radiation would become trapped and so not contribute to the measurement. There is nothing in the general design of the cavity which limits the approach to the detection of a single gaseous species (with or without the additional use of a reference channel). The number, size and shape of the openings and how they are positioned may be used to increase the number of gases that may be sensed simultaneously by adding detectors provided with filters giving selectivity toward the appropriate wavelength range and/or additional sources.

Cylindrical cavities are known to support "whispering modes", predominantly characterised by annular propagation around the cavity perimeter. By positioning openings allowing the capture or otherwise of such modes by the detector, the optical designer is provided with a further degree of freedom which may significantly impact the effective pathlength of the system. In the design described here, the cavity opening positions have not been chosen to favour the capture of such modes.

In the preferred implementation there are three circular holes in the disc forming the base of the cavity. One admits electromagnetic radiation from a single source and two allow electromagnetic radiation that has interacted with the gas to leave the cavity for detection by a suitable radiation detector. This arrangement is suitable for single gas dual beam NDIR gas sensing applications.

(3) The range of angles of incidence of radiation reaching the optical filter.

The illuminating angle exerts a significant influence upon the behaviour of optical filters according to known principles. Thus, changes in the detector aperture size and field of view can be used to alter the pathlength without changes to the mechanical design of the cavity.

(4) The reflectivity and stability of the optical cavity surface.

Changes in reflectivity produced by surface degradation or obscuration are often most severe in particular ranges of angle of incidence due to the relationship between angle of incidence and number of wall reflections in this design. By utilising a wide range of such angles but keeping the number of wall reflections nearly constant in a non-focussing design, the impact of such effects can be mitigated.

Path length and angle of incidence considerations are to some extent independent of each other but are connected through the angular dependence, bandwidth and centre wavelength of the filter, the field of view of the detector and the direction in which the detector is pointing. In principle this complex set of relationships may be manipulated to alter the performance of the device. In the implementation described here, the detector points along the cylindrical axis and is symmetrically offset from the centre. In this system, a range of paths and pathlengths through. the gas are able to contribute to the useful signal at the detector.

We recognize that optical gas sensors of this type will usually require individual calibration or scaling, even when the design is sufficiently robust to permit the use of generic linearisation and thermal compensation algorithms. These coefficient differences primarily arise from the variable properties of (a) the interference filters used to select wavelengths of interest from the broadband source and (b) the IR detector element(s) themselves. Applications demanding higher performance may require individual device calibration at 3 or more temperatures. This is time consuming and expensive for the instrument manufacturer (especially in systems where there are multiple sensors with differing lifetimes) and requires that the sensor head and electronics be maintained together throughout the sensor life. Field replacement becomes very difficult in such circumstances.

A preferred approach is for the sensor manufacturer to supply every device with the relevant information permanently embedded within it, solving the problem of inter device variation without user intervention. Such data is readily obtained by the sensor manufacturer on many devices simultaneously. In order to allow storage and retrieval of such information, an EEPROM is preferably incorporated within the (flameproof) sensor housing which communicates through the existing analogue connection pins without the need for an additional dedicated digital lines. This may hold the necessary linearisation and correction parameters, in addition to other useful information such as the device type, manufacturing details, warranty date and serial number.

In some implementations, the electromagnetic radiation is generated inside the cavity by placing one or more sources within it. The sources may be a heated material or wire within a transparent enclosure. The material may be heated by an electric current passing through the material itself or a heater bonded to it or by other heating mechanisms (e.g. radiative). The source(s) will then generate (infra-red) radiation. The radiation detectors may be placed within the cavity or outside the cavity behind a window(s). Alternatively, the gas within the cavity may itself be heated to act as its own source of radiation.

Examples of suitable sources include filament bulbs, other grey/black body sources, LEDs, and lasers. Lamps or filament bulbs are substantially isotropic in the forward hemisphere, but the source could be Lambertian (flat surface). In the case of LEDs, although these would usually have much narrower emission bandwidths than the grey or black bodies mentioned above, they might still be configured to have a bandwidth relatively large in comparison with the bandpass of an interference filter used to select a particular spectral region.

A physical property of the gas such as temperature or pressure may be detected as a measurement of the radiation absorbed by the gas within the cavity.

In accordance with a second aspect of the present invention, a method of constructing a gas sensor, the method comprises:

(a) inserting a tubular, optical housing, closed by a wall at one end except for at least one gas access aperture, into a tubular outer housing closed at its end adjacent the closed end of the optical housing, except for at least one gas access opening;

(b) inserting a radiation source and detector on a printed circuit board into a tubular electronics housing, the electronics housing having an end wall closed at one end except for one or more apertures to allow access to the source and detector;

(c) inserting the electronics housing into the outer housing so that it mates with the optical housing and defines therewith a substantially closed optical cavity between the end walls of the electronics and optical housings and in which a gas to be sensed is located in use; and, (d) securing the assembled housings together.

An example of a sensor and method according to the present invention will now be described with reference to the accompanying drawings, in which:—

The primary purposes of the design to be described are to;

(i) maximise the available optical path with a minimum of reflections within an industry standard "4-series" housing;

(ii) be simply and easily constructed, (potentially in an automated process), having a low part count;

(iii) be capable of flameproof certification;

(iv) have low cost.

Figure 1:
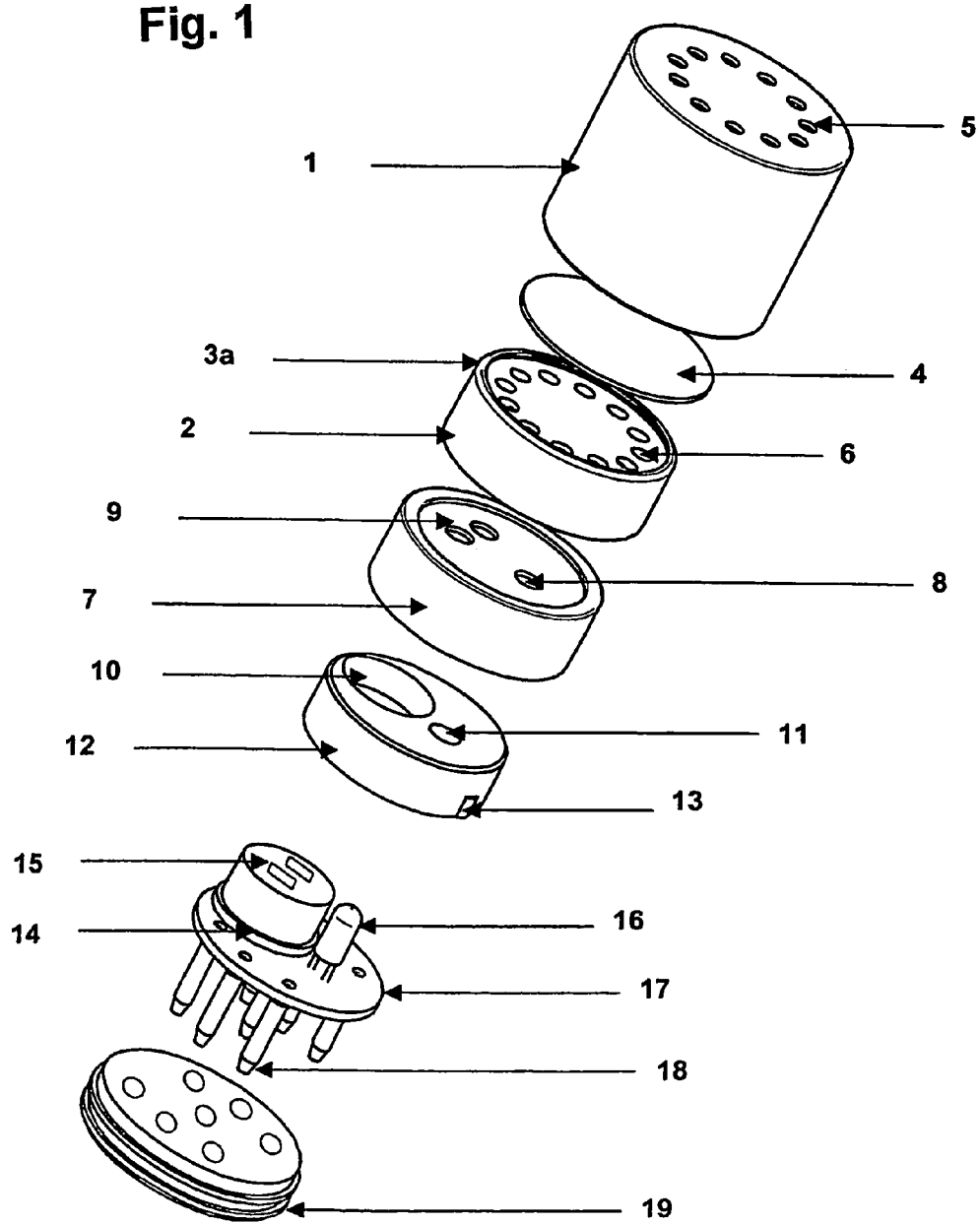
FIG. 1 shows the sensor in exploded form.

The favoured design shown in FIGS. 1 and 2 employs machined metal parts for the optical housing, the electronics housing and the outer casing although the use of alternative materials is considered later. Metal has some advantages in terms of ease of certification and in even quite significant volumes, there is no cost penalty over the use of moulded parts. Metal fabrication techniques other than machining as envisaged here (e.g. injection metal moulding) could also be employed.

The description applies to sensors for the detection of $CO_2$ in the 0-5% concentration range, although with appropriate choice of optical filters and/or different optical chamber dimensions, different concentration ranges and/or gas species (e.g. hydrocarbons) may be detected.

The outer casing 1 is a cylindrical can with gas diffusion access apertures 5 annularly distributed on its upper face. The positioning of the apertures is chosen so that there is adequate space for a gas seal (e.g. via an O ring or gasket) to be made outside the aperture ring between the upper face and the casing of an instrument (not shown) should this be desired. Casing 1 is manufactured from stainless steel 304 to BS970 and its primary functions are (a) to protect the internal parts of the sensor; (b) provide means for gas to access the interior; (c) form (in conjunction with the internal components) a flame path from the interior to the exterior, and (d) to provide a key for the potting compound with which the base of the sensor is finally sealed. The inner bore of the casing 1 is toleranced to 18+0.0/−0.025 mm and the thickness of top of the can is at least 0.4 mm to aid machining. The casing is additionally provided with two annular grooves 31 on the internal surface near the base into which the potting compound 19 is keyed on final assembly.

If required, a porous membrane (not shown) of PTFE or similar material may be applied to the outer or inner plane surface of the outer casing 1 to help prevent the ingress of dust, water droplets or liquids.

An optical housing 2 is cylindrical and is made from stainless steel 304 to BS 970, additionally provided with hard acid gold plated 1 micron thick over 2 micron electroless nickel. The part is toleranced to 17.75+0.025/−0.0 mm to ensure that on assembly (by insertion into outer casing 1), the maximum annular flame path between the two does not exceed 50 microns, thereby complying with certification requirements. The gold plating ensures that the internal surface of the component 2, which forms the upper section of an optical cavity or chamber 32, offers adequate reflective performance in the IR wavelength region of interest (2-6 microns). The main properties required are high reflectivity >95% and long term stability of this value. The surface may be specularly reflective or diffuse which would have the advantage of scattering the reflected radiation and thereby improving its uniformity. IR reflective coatings other than gold could be employed, and polishing of the inner metal surfaces might also be acceptable. It is important that the surface is robust and offers long life without degradation such as might be caused by corrosion commencing at pinhole imperfections. The surface may be covered in an IR transparent protective coating to provide additional reflective efficiency and assurance. The optical cavity 32 in this case has an internal diameter of 11.95+/−0.05 mm and a height of 5.5+/−0.05 mm, although even without altering the external dimensions of the optical housing 2, the internal dimensions may be varied to some extent, for the purposes of detecting other gases or to allow different concentration ranges to be addressed.

In this particular example, therefore, the cavity has a height to width ratio of approximately 0.46. Cavities of such dimensions have been found to provide good uniformity of radiation, resulting in enhanced sensor performance. However, the cavity could be any shape provided substantially uniform illumination were achieved.

The optical housing 2 has gas diffusion access apertures 6 in its upper face. These are of a number and distribution such that their disposition relative to apertures 5 in the outer casing 1 has a minimal effect upon the response time of the system. This eases assembly processes by removing any annular alignment requirement on the insertion of housing 2 into casing 1. The 1.5 mm diameter holes 6 are only half cut into the optical chamber to maximize the available reflective surface. The region where the side and top faces of the housing 2 meet tends to act as a trap for radiation and so contributes comparatively little to the net throughput from the source to the detector. Thus, gas access to the sensor may be through the top face (as preferred by instrumentation manufacturers) whilst simultaneously minimizing the impact of the apertures 6 in reducing the available reflective surface area.

The optical housing 2 is also required in this example to retain a flame arresting mesh 4 which is an integral part of the flameproofing arrangements in the design. The function of the mesh 4 is to meet the flame transmission and explosion testing requirements of certification authorities by arresting any explosion/flame emanating from within the sensor. In this case we employ one layer of Dutch twill weave mesh, 0.4 mm thick, (Potter & Soar) although additional layers (or sinter materials) could readily be incorporated with appropriate dimensional changes to the assembly. The mesh is retained by peening into the top face of the optical chamber 2 using a raised lip (3a in FIG. 1) provided for this purpose. In FIG. 2, the lip is shown in the assembled position 3b. In addition to tightly retaining the mesh 4, the resulting lip also creates a thin mixing chamber 30 around 0.2 mm in height. Gas enters this area after diffusing through the apertures 5 in the outer casing 1, before passing through the mesh 4 and entering the optical chamber 32. The presence of this small void 30 further ensures that there is minimal dependence of the overall system response time upon the relative annular orientations of the outer casing and the optical chamber;

Of course, it will be readily apparent that a sensor utilizing uniform radiation, in the manner described, could be constructed without the components required to achieve the certification standard. This may be preferable in situations where only non-combustible gases are to be detected, for example. In such cases, the sensor may be built without a flame arrester (mesh 4), and/or there may be less potting compound.

In this example, the base uses the full available diameter, the upper optical cavity within the housing 2 has a slightly reduced diameter (12 mm as opposed to 15 mm). This reduced diameter does not produce a significant degradation in behaviour, whilst the smaller surface area and higher signal levels are beneficial. However, both versions offer acceptable performance in the intended application. It will be noted, by reference to FIG. 2, that the side wall thickness of the housing 2 is substantially greater than that of the electronics housing 7. This is not essential from a constructional or certification point of view—both could be made to the same thickness, which would result in an internal diameter for the optical cavity of 15 mm rather than the nominal 12 mm as shown here. However, as noted, there are some minor performance advantages (for example the faster filling time of a smaller gas chamber volume leads to quicker sensor response/recovery) and no major drawbacks to the approach chosen.

It should also be noted that for gases requiring a different pathlength, one approach would be to use the 15 mm diameter cavity as discussed above and change the positions of the source and detector apertures relative to the central axis. These changes could be achieved with no external modification to the sensor dimensions and would still allow certification to be obtained.

An optical IR source 16 and a detector 14 are mounted on a pcb 17 together with connection pins 18. The source in this example is a conventional filament bulb (MG&G 4560-01) although other forms of grey/black body source or solid state emitters could also be employed. We have used pyroelectric detectors in this example (e.g. InfraTec LIM122 or Perkin Elmer LHi814) provided with appropriate wavelength selective filters for the target gas of choice, but semiconductor devices or bolometers are also feasible alternatives. The detector 14 used here is a two-channel device, having different wavelength-selective interference filter windows 15 over each element, in order to create signal and reference channels. However, single channel detectors may be employed for uncompensated systems, or larger numbers of elements can be used to detect multiple species or provide more sophisticated compensation options. Also, separate detectors can be used for the signal and reference channels. A thermistor (e.g. Betatherm SMD33KF410HT—not shown) may be attached to the pcb 17, (preferably in close proximity to the detector 14, since this is the primary source of temperature sensitivity) in order to provide the temperature data required for thermal compensation.

In the present design, we have also incorporated an EEPROM (Dallas D52430AP—not shown) on the pcb 17 in order to store information about the sensor and thereby provide enhanced functionality for the user. In order to minimize costs, we have not adopted a more sophisticated (but feasible) approach employing an on board microprocessor to provide a fully processed sensor output. Since modern instruments invariably use an external processor to undertake a multitude of data acquisition, processing and display functions, we propose that such external processors perform the necessary calculations. The EEPROM uses connection pins 18 for communication during the warm-up period via modulation of a power rail voltage immediately after power on and requires no dedicated digital connections. This approach offers designers the maximum degree of freedom in system integration.

Raw data from the detector channel(s), the thermistor output, and the relevant coefficients downloaded from memory, when externally processed, provide a fully linearised and temperature compensated output. The EEPROM may also store other information of relevance (manufacture date, range, warranty period etc.), although the facilities offered by packages small enough to be integrated within the sensor housing itself are limited. The ability to permanently associate information with the sensor within the flameproof enclosure is a key benefit to users, especially when undertaking sensor replacements in the field. It is also possible to configure some of the memory to allow user-written calibrations or other data to be stored on board.

A bung 12 fits over the components which protrude from the pcb 17. PTFE is the preferred material for the bung, which would normally be moulded; however polypropylene may be substituted to reduce costs if other constraints permit. The primary function of the bung 12 is to reduce the free internal volume of the assembled sensor, since in the preferred design there are no windows separating the optical components 14,16 from the gas chamber 32. Without the bung 12, spaces between and around the source 16 and detector 14 would gradually become filled with gas on extended exposure, potentially increasing the response time of the system. Conversely, gas trapped in these regions could slowly diffuse back out into the optical path, thereby increasing the recovery time of the device on returning to a notionally clean atmosphere. Of course if windows are provided between the gas chamber 32 and optical components, close fitting is not necessary.

A further important consideration is that reduction of the free volume within the sensor significantly reduces the overpressure which can be generated by an ignition of combustible gas within the device, and which the chamber 32 must therefore be able to sustain without damage. This in turn eases the constraints upon the strength demanded of the assembly and allows much more flexibility in the design of the housing components, and reduces cost and complexity.

Bung 12 also fulfils other important purposes. It is toleranced to provide a close fit around the optical components 14,16 on the pcb 17, and as such helps to maintain their alignment and provides protection during assembly processes. It is intended that the bung would be put in place as soon as the pcb assembly was complete, so that this component could be shipped with confidence. Apertures 10 and 11 are provided so that the detector 14 and source 16 are not obscured. The bung 12 also acts as a partial seal to potting compound 19 which might otherwise seep into the optical chamber 32 on final assembly of the device. The seals between the bung 12, detector 14, source 16 and an electronics housing 7 may be formed (for example) by creating annular flexible features on appropriate surfaces of the bung as part of the moulding process. Although in the present assembly the ability of the bung to retain pcb 17 in position after insertion into the electronics housing 7 is not critical (since no inversion of the assembly is necessary until after the potting compound 19 has been added and cured), there are other possible assembly routes in which such additional functionality of the bung may be of considerable benefit. The bung may also be provided with a feature 13 which mates with a locating feature (not shown) on the electronics housing 7 to ensure that the pcb assembly fits in the correct orientation. Although this feature could be omitted in the design shown here (since the bulb can only protrude into the optical chamber when fitted in the correct orientation), the presence of an additional keying feature can help to prevent accidental damage during assembly.

Figure 2:
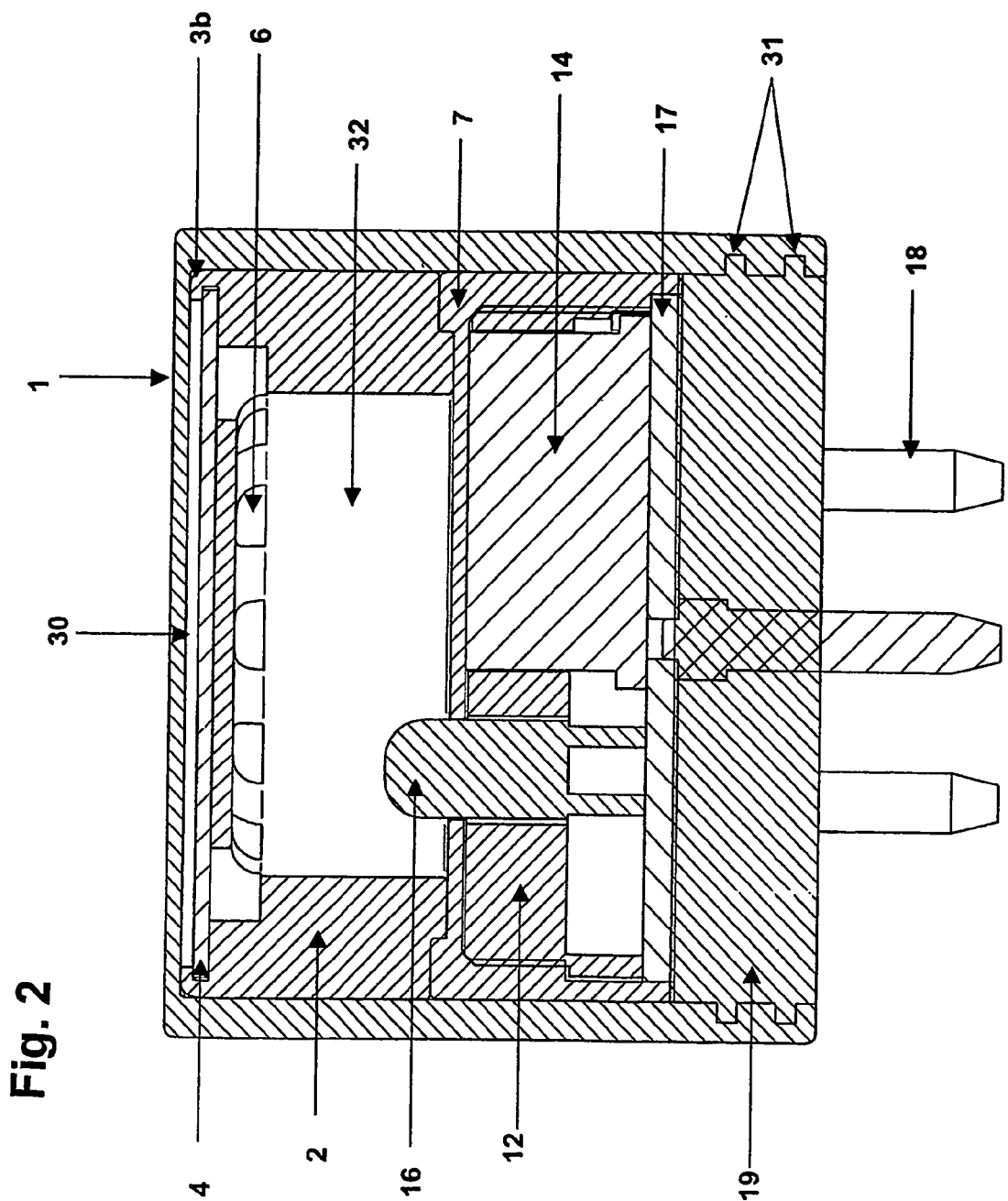
FIG. 2 is a cross section of the sensor in its fully assembled form.

The bung/pcb assembly fits into the electronics housing 7 as shown in FIG. 2. The electronics housing 7 is manufactured from stainless steel 304, and is provided with the same gold plating as the optical chamber 2. Source 16 protrudes through aperture 8 in the upper half of the housing 7 and into the optical chamber 32 once the assembly is complete, whilst the detector windows 15 view the optical chamber 32 through apertures 9. It should be noted that it would in fact be preferable, in terms of approximating the cavity to an ideal integrating sphere, to position both the source and the detector outside the cavity. However, for practical reasons it may be necessary to allow the source envelope to protrude into the cavity (as in the present embodiment). Such effects should be minimized wherever possible. The electronics housing 7 provides the plane base reflective surface of the optical chamber 32, retains the pcb 17 at the correct height and forms part of the flamepath between the inner and outer sections of the casing 1 by virtue of the outer diameter being toleranced to 19.75+0.025/−0.0 mm. Unlike many IR sensor designs there are no transparent windows to isolate the source 16 and detector 14 from the gas sample, which significantly reduces costs and eases assembly. In order to ensure a good seal between the pcb 17 and electronics housing 7, a bead of cyanoacrylate adhesive is injected onto the ledge against which pcb 17 rests in the assembled device. This provides further insurance against any leakage of potting compound past this interface.

Flange features at the base of the optical housing 2 and on the top of the electronics housing 7 ensure that the two mate together correctly, as shown in FIG. 2. 3.5 mm of potting compound 19 is applied to the rear of the sensor to complete the assembly and provide the strength required to maintain housing integrity in the event of an internal ignition. Suitable materials are Stycast 2651 or 2850, manufactured by Emerson Cumming, or Araldite HY956/CW2248.

The overall assembly process therefore consists of a small number of simple steps—
(a) Insert optical housing 2 with attached mesh 4 into outer casing 1;
(b) Insert populated pcb/bung 17,12 into electronics housing 7 and seal with adhesive;
(c) Insert electronics housing 7 into outer casing 1 to mate with optical housing 2;
(d) Apply potting compound 19 to finally retain all inner components.

The insertion processes may be performed by hand, although given the tight tolerances in some cases, a mechanical press may be useful in preventing binding between the metal components.

There are a number of alternative approaches to the materials selected in the above example. Different types of metal may be used for the optical, electronic and outer casings, although the requirement for ease of machining and the demands of certification approvals will limit the available range. We have also built devices employing plastic outer casings, and there is no difficulty in principle in employing all-plastic construction for the casing, optical and electronic chambers. Suitable materials are liquid crystal polymer (LCP) or poly phenylene sulphide (PPS). The required reflective finish can be produced on plastic, provided that appropriate processing is employed. A further possibility offered by the use of plastic parts is the overmoulding of some components. For example, metal optical surfaces could be overmoulded to form the outer casing. This has the advantage of eliminating the flame path which exists between the inner and outer surfaces in the example here and might also allow elimination of the potting step. However, the use of plastic components may affect the prospects of obtaining flameproof certification.

Different gas species and concentration ranges produce varying degrees of optical absorption and so may require significantly different pathlengths for optimum performance. The use of two parts to create the optical cavity 32 allows the effective pathlength to be increased by changing the optical housing 2 (only) to a longer (or larger diameter) component. Alternatively, placing the source 16 and detector 14 further towards the perimeter of the cavity 32 can increase the pathlength. Conversely, the pathlength may be reduced by making opposite changes, or by employing the same optical envelope but reducing the reflectivity of parts or all of the wall surface. Of course, such an approach also represents a potential further deviation from the ideal spherical cavity. For example, the use of non-reflective (or "blackened") sections within the cavity might enhance the intensity of "whispering modes". This could be useful if such modes were deemed to be an effective means of operation. Blackening can also be used to "tune" the reflection characteristics of a cavity. For example, in a cavity which produces imperfect radiation uniformity, perhaps as a result of its shape owing to design constraints, well-positioned blackened portions can improve the uniformity in certain. regions. However, the use of non-reflective portions needs to be considered carefully and a compromise reached between enhancement of useful modes and the effect on the uniformity of the radiation. It will be necessary to consider the details of the particular sensor design to determine the effect that blackening will have on its performance. In general, the ability to introduce such changes with only minor modifications to the design is advantageous when attempting to produce a family of sensors for different species conforming to a standard package size.

Electrical connections to and from the sensor are made via pins 8 in the present example, primarily to maintain compatibility with existing commercially available devices and so ease the integration of the improved sensor into existing instrumentation. However, such connection means are relatively space inefficient and alternative methods might be preferable in order to maximize the fraction of the internal volume available for use as an optical path. One possible route to achieve this is the use of overmoulded lead frames to replace some or all of the internal pcb and the use of output pads instead of pins. Direct encapsulation of a lead frame in this way can produce a highly effective flameproof enclosure.

This design provides a robust optical gas sensing arrangement, which offers good inter-device reproducibility and stability against changes affecting the wavelength-dependent properties of key components. The sensor is simply assembled from a small number of components and requires minimal alignment. It offers pin compatibility with existing commercial sensors; but also offers access to valuable extra facilities via the on board EEPROM and appropriate interrogation circuitry.

The invention claimed is:

1. A gas sensor comprising a cavity for containing a gas; means for generating radiation which is transmitted through the cavity and including one or more wavelengths which is absorbed in use by a gas to be detected; and a detector for detecting radiation which has passed through the cavity, the detector having a surface area which is visible to the interior of the cavity, wherein the radiation generating means and/or detector(s) is mounted on a printed circuit board (PCB) and is surrounded by resilient protection comprising a resilient member having one or more apertures through which the radiation means and/or respective detector(s) extend; and the resilient member, the PCB and the components mounted thereon are located in an electronics housing having an upper wall, the upper surface of which defines a wall of the cavity, the resilient member extending from the PCB to the lower surface of the upper wall of the electronics housing such that free volume therewithin is reduced.

2. A sensor according to claim 1, wherein the radiation generating means and/or respective detector(s) extends in a close fitting relationship through the aperture(s).

3. A sensor according to claim 1, wherein the resilient member and electronics housing have complementary keying features which interengage.

4. A gas sensor according to claim 1, wherein the cavity comprises a first end wall adjacent to which at least one of the means for generating radiation and the detector is positioned, a second end wall which opposes the first end wall, and a side wall; the first and second end walls defining the height of the cavity between them and the width of the cavity being defined as a maximum dimension of the cavity orthogonal to its height, wherein the ratio of the height to the width is greater than or equal to 0.1 and less than 0.7.

5. A gas sensor according to claim 1, wherein the entire visible surface area of the detector is illuminated with substantially unfocussed radiation.

6. A gas sensor according to claim 1, wherein increasing the visible surface area of the detector relative to the surface area of the cavity walls increases the signal to noise ratio detected by the detector.

7. A sensor according to claim 1, wherein the radiation generating means generates infra-red radiation.

8. A sensor according to 1, wherein the radiation generating means comprises a heating element to heat gas within the cavity so as to cause the gas to generate infra-red radiation.

9. A sensor according to claim 1, further comprising one or more additional radiation detectors, each detector being adapted to sense radiation centered on a respective, different wavelength.

10. A sensor according to claim 1, wherein the cavity wall defines a window allowing radiation to pass therethrough to the or a respective detector.

11. A sensor according to claim 1, wherein a majority, preferably more than 90% of the cavity walls have a reflectivity to radiation exceeding 95%.

12. A sensor according to claim 1, wherein at least a portion of the cavity walls are provided with a reflective coating.

13. A sensor according to claim 12, wherein the reflective coating comprises gold plating.

14. A sensor according to claim 1, wherein the cavity walls are covered by a radiation transparent protective coating.

15. A sensor according to claim 1, wherein the cavity is tubular, for example cylindrical, and has substantially planar end walls.

16. A sensor according to claim 1, where the means for generating radiation, and detector are located within an outer housing having at least one aperture to allow gas to enter.

17. A sensor according to claim 16, further comprising a flame arrestor within the outer housing.

18. A sensor according to claim 17, wherein the flame arrestor is secured to an outer surface of a housing having at least one aperture, the housing defining a wall of the cavity, by a raised lip which overlaps the flame arrestor, whereby when the cavity housing is assembled in the outer housing, the raised lip defines the thickness of a gas chamber communicating with the apertures in the outer and cavity housings.

19. A gas sensor comprising a cavity for containing a gas; means for generating radiation which is transmitted through the cavity and including one or more wavelengths which is absorbed in use by a gas to be detected; and a detector for detecting radiation which has passed through the cavity, the detector having a surface area which is visible to the interior of the cavity, the walls of the cavity being sufficiently reflective to the radiation that the cavity is substantially uniformly illuminated with the radiation, wherein the cavity is tubular, for example cylindrical, and has substantially planar end walls, adjacent to at least one of which, at least one of the means for generating radiation and the detector is positioned and wherein the ratio of the height to the width of the cavity is greater than or equal to 0.1 and less than or equal to 0.7.

20. A sensor according to claim 19, wherein the height to width ratio is greater than or equal to 0.2 and less than or equal to 0.7.

21. A sensor according to claim 20, wherein the height to width ratio is greater than or equal to 0.4 and less than or equal to 0.7.

22. A sensor according to claim 21, wherein the height to width ratio is greater than or equal to 0.5 and less than or equal to 0.7.

23. A sensor according to claim 19, wherein the visible surface of the detector is illuminated with substantially unfocussed radiation.

24. A gas sensor according to claim 19, wherein the entire visible surface area of the detector is illuminated with substantially unfocussed radiation.

25. A gas sensor according to claim 19, wherein increasing the visible surface area of the detector relative to the surface area of the cavity walls increases the signal to noise ratio detected by the detector.

26. A sensor according to claim 19, wherein the radiation generating means and/or detector(s) is mounted on a printed circuit board and is surrounded by resilient protection.

27. A sensor according to claim 26, wherein the resilient protection comprises a resilient member having one or more apertures through which the radiation generating means and/or respective detector(s) extends.

28. A sensor according to claim 27, wherein the radiation generating means and/or respective detector(s) extends in a close fitting relationship through the aperture(s).

29. A sensor according to claim 26, wherein the PCB and the components mounted thereon are located in an electronics housing having an upper wall, the upper surface of which defines a wall of the cavity.

30. A sensor according to claim 27, wherein the resilient member and electronics housing have complementary keying features which interengage.

31. A sensor according to claim 19, wherein the radiation generating means generates infra-red radiation.

32. A sensor according to claim 31, wherein the infra-red radiation generating means comprises a heating element to heat gas within the cavity so as to cause the gas to generate infra-red radiation.

33. A sensor according to claim 19, further comprising one or more additional radiation detectors, each detector being adapted to sense radiation centered on a respective, different wavelength.

34. A sensor according to claim 19, wherein the cavity wall defines a window allowing radiation to pass therethrough to the or a respective detector.

35. A sensor according to claim 19, wherein a majority, preferably more than 90% of the cavity walls have a reflectivity to radiation exceeding 95%.

36. A sensor according to any of claim 19, wherein at least a portion of the cavity walls are provided with a reflective coating.

37. A sensor according to claim 36, wherein the reflective coating comprises gold plating.

38. A sensor according to claim 19, wherein the cavity walls are covered by a radiation transparent protective coating.

39. A sensor, according to claim 19, wherein the cavity, means for generating radiation, and detector are located within an outer housing having at least one aperture to allow gas to enter.

40. A sensor according to claim 39, further comprising a flame arrestor within the outer housing.

41. A sensor according to claim 40, wherein the flame arrestor is secured to an outer surface of a housing having at least one aperture, the housing defining a wall of the cavity, by a raised lip which overlaps the flame arrestor whereby, when the cavity housing is assembled in the outer housing, the raised lip defines the thickness of a gas chamber communicating with the apertures in the outer and cavity housings.

42. A method of constructing a gas sensor, the method comprising:
   (a) inserting a tubular, optical housing, closed by a wall at one end except for at least one gas access aperture, into a tubular outer housing closed at its end adjacent the closed end of the optical housing, except for at least one gas access opening;
   (b1) fitting a resilient member over a radiation source and detector on a printed circuit board (PCB), the resilient member having one or more apertures through which the radiation means and/or respective detector(s) extend;
   (b2) inserting the so-assembled resilient member, radiation source detector and printed circuit board into a tubular electronics housing, the electronics housing having an end wall closed at one end except for one or more apertures to allow access to the source and detector, the resilient member extending from the PCB to the lower surface of the upper wall of the electronics housing such that free volume therewithin is reduced;
   (c) inserting the electronics housing into the outer housing so that it mates with the optical housing and defines therewith a substantially closed optical cavity between the end walls of the electronics and optical housings and in which a gas to be sensed is located in use, the end wall of the electronics housing forming a wall of the cavity; and
   (d) securing the assembled housings together.

43. A method according to claim 42, wherein step (d) comprises applying potting compound to the assembled housings.

44. A method of constructing a gas sensor according to claim 19, the method comprising:
   (a) inserting a tubular, optical housing, closed by a wall at one end except for at least one gas access aperture, into a tubular outer housing closed at its end adjacent the closed end of the optical housing, except for at least one gas access opening;
   (b) inserting a radiation source and detector on a printed circuit board into a tubular electronics housing, the electronics housing having an end wall closed at one end except for one or more apertures to allow access to the source and detector;
   (c) inserting the electronics housing into the outer housing so that it mates with the optical housing and defines therewith a substantially closed optical cavity between the end walls of the electronics and optical housings and in which a gas to be sensed is located in use; and, (d) securing the assembled housings together.

45. A method according to claim 44, wherein step (d) comprises applying potting compound to the assembled housings.

46. A method according to claim 42 for constructing a gas sensor comprising a cavity for containing a gas; means for generating radiation which is transmitted through the cavity and including one or more wavelengths which is absorbed in use by a gas to be detected; and a detector for detecting radiation which has passed through the cavity, the detector having a surface area which is visible to the interior of the cavity, wherein the radiation generating means and/or detector(s) is mounted on a printed circuit board (PCB) and is surrounded by resilient protection comprising a resilient member having one or more apertures through which the radiation means and/or respective detector(s) extend; and the resilient member, the PCB and the components mounted thereon are located in an electronics housing having an upper wall, the upper surface of which defines a wall of the cavity, the resilient member extending from the PCB to the upper wall of the electronics housing such that free volume therewithin is reduced.

* * * * *